United States Patent [19]

Schönafinger et al.

[11] Patent Number: 5,679,704
[45] Date of Patent: Oct. 21, 1997

[54] USE OF 2-(N-(2-AMINOETHYL)AMINO) ACETIC ACID DERIVATIVES

[75] Inventors: Karl Schönafinger, Alzenau; Ursula Schindler, Bad Soden; Eckhard Schraven, Frankfurt am Main, all of Germany

[73] Assignee: Cassella Aktiengesellschaft, Frankfurt am Main, Germany

[21] Appl. No.: 543,395

[22] Filed: Oct. 16, 1995

Related U.S. Application Data

[62] Division of Ser. No. 337,051, Nov. 10, 1994, Pat. No. 5,500,436, which is a continuation of Ser. No. 89,780, Jul. 9, 1993, abandoned.

[30] Foreign Application Priority Data

Jul. 13, 1992 [DE] Germany ............... 42 22 980.4

[51] Int. Cl.⁶ ............ A61K 31/44; A61K 31/38; A61K 31/415; A61K 31/34
[52] U.S. Cl. ............ 514/438; 514/397; 514/401; 514/408; 514/438; 514/439; 514/461; 514/564
[58] Field of Search ............ 514/397, 401, 514/408, 438, 439, 461, 564

*Primary Examiner*—Theodore J. Criares
*Attorney, Agent, or Firm*—Perman & Green, LLP

[57] ABSTRACT

The invention relates to the use of 2-(N-(2-aminoethyl)amino)acetic acid derivatives of the formula I $$R-\underset{\underset{COOH}{|}}{CH}-NH-CH_2-CH_2-NH_2 \qquad I$$

in which

R denotes, for example, phenyl or thienyl, and their pharmacologically acceptable acid addition salts as pharmacological active compounds.

3 Claims, No Drawings

USE OF 2- (N-(2-AMINOETHYL)AMINO) ACETIC ACID DERIVATIVES

This is a divisional of application Ser. No. 08/337,051 filed on Nov. 10, 1994, now U.S. Pat. No. 5,500,436, which is a continuation of Ser. No. 08/089,780 filed on Jul. 9, 1993 now abandoned.

The invention relates to the use of 2-(N-(2-aminoethyl) amino)acetic acid derivatives of the formula I

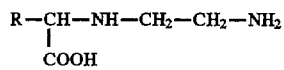

in which

R denotes phenyl, thienyl, furyl, pyridyl, pyrrolyl, imidazolyl or thiazolyl, or phenyl, thienyl, furyl, pyridyl, pyrrolyl, imidazolyl or thiazolyl which is monostituted or polysubstituted by halogen, alkyl, alkoxy, dialkylaminoalkoxy or alkoxyalkoxy, and their pharmacologically acceptable acid addition salts as pharmacological active compounds, in particular for the control and prevention of defects or disorders which are caused by non-enzymatic glycosylation.

The invention also relates to the use of the compounds of the formula I and their pharmacologically acceptable acid addition salts as pharmacological active compounds for the production of pharmaceutical preparations.

The invention also relates to pharmaceutical preparations which contain one or more compounds of the formula I and/or one or more pharmacologically acceptable acid addition salts thereof as active compounds.

The phenyl, thienyl, furyl, pyridyl, pyrrolyl, imidazolyl or thiazolyl radicals representing R can also be monosubstituted or polysubstituted by halogen, alkyl, alkoxy, dialkylaminoalkoxy and/or alkoxyalkoxy. In this case, a phenyl radical can preferably be monosubstituted, disubstituted or trisubstituted. If substituted, the other radicals representing R are preferably monosubstituted, in particular by alkyl or alkoxy. In the case of multiple substitution, the substituents can be identical or different.

Halogen in particular represents fluorine, chlorine, bromine and iodine, of which fluorine and chlorine are preferred. Alkyl and alkoxy radicals, even in combination with the other substituents, can be straight-chain or branched.

Preferred alkyl is $(C_1-C_4)$alkyl. Preferred alkoxy is $(C_1-C_4)$alkoxy. Preferred dialkylaminoalkoxy is di$(C_1-C_4)$ alkylamino-$(C_1-C_4)$alkoxy. Preferred alkoxyalkoxy is $(C_1-C_4)$alkoxy-$(C_1-C_4)$alkoxy.

The thienyl radical representing R is preferably a 2-thienyl radical. The pyridyl radical representing R is preferably a 3-pyridyl radical. The furyl radical representing R is preferably a 2-furyl radical. The pyrrolyl radical representing R is preferably a 2-pyrrolyl radical. The imidazolyl radical representing R is preferably a 5-imidazolyl radical. The thiazolyl radical representing R is preferably a 4-thiazolyl radical.

Preferred radicals R in formula I are: phenyl, 4-methoxyphenyl, 4-fluorophenyl, 4-chlorophenyl, 3,4-dimethoxyphenyl, 3,4,5-trimethoxyphenyl, 4-(diethyl) aminoethoxy)phenyl, 4-(methoxyethoxy)phenyl, 3-pyridyl, 2-furyl, 1-methylimidazol-5-yl, thiazol-4-yl, 2-methylthien-5-yl and 1-methylpyrrol-2-yl. 2-thienyl is particularly preferred for R.

Of the compounds of the formula I, the following are preferably used in the context of the present invention:

2-(N-(2-aminoethyl)amino)-2-(4-(2-diethylamino-ethoxy) phenyl)-acetic acid dihydrochloride, 2-(N-(2-aminoethyl)amino)-2-(4-fluorophenyl)acetic acid dihydrochloride, 2-(N-(2-aminoethyl)amino)-2-(4-methoxyphenyl)acetic acid dihydrochloride, 2-(N-(2-aminoethyl)amino)-2-(3,4,5-trimethoxyphenyl) acetic acid dihydrochloride, 2-(N-(2-aminoethyl)amino)-2-(3-pyridyl)acetic acid dihydrochloride, 2-(N-(2-aminoethyl)amino)-2-(4-chlorophenyl)acetic acid dihydrochloride, 2-(N-(2-aminoethyl)amino)-2-(2-furyl)acetic acid dihydrochloride, 2-(N-(2-aminoethyl)amino)-2-(1-methylimidazol-5-yl) acetic acid trihydrochloride, 2-(N-(2-aminoethyl)amino)-2-(4-thiazolyl)acetic acid dihydrochloride, 2-(N-(2-aminoethyl)amino)-2-(2-methylthien-5-yl)acetic acid dihydrochloride, 2-(N-(2-aminoethyl)amino)-2-(1-methylpyrrol-2-yl)acetic acid dihydrochloride, 2-(N-(2-aminoethyl)amino)-2-(4-(2-methoxyethoxy) phenyl)acetic acid dihydrochloride, 2-(N-(2-aminoethyl)amino)-2-(3,4-dimethoxyphenyl)acetic acid dihydrochloride, 2-(N-(2-aminoethyl)amino)-2-(phenyl)acetic acid dihydrochloride.

In the context of the present invention, the compound 2-(N-(2-aminoethyl)amino)-2-(2-thienyl)acetic acid dihydrochloride is particularly preferably used.

Since the compounds of the formula I contain both an acidic carboxyl group and two basic groups in the molecule, they are zwitterionic compounds, which can form internal salts. The compounds of the formula I, however, can also form salts with other inorganic and organic acids.

Suitable acids are, for example, hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulfamic, phenylpropionic, gluconic, ascorbic, isonicotinic, methanesulphonic, p-toluenesulphonic, citric or adipic acid. Pharmacologically acceptable acid addition salts are preferred. The acid addition salts can be prepared in the customary manner by combining the components, expediently in a suitable solvent or diluent.

Some of the compounds of the formula I are already known as intermediates for the preparation of 2-imidazolinylacetic acid derivatives having cardiovascular activity (compare Arzneimittel-Forsch./Drug Res. 35 (I), 1 (1985), Table 1 and DE-A1-3,329,028, Examples 1b, 2b, 4b, 9 to 20).

Surprisingly, it has now been found that the compounds of the formula I and their pharmacologically acceptable acid addition salts are pharmacologically active themselves. They are able to prevent or to decrease, i.e., for example, to suppress or at least favourably to affect non-enzymatic glycosylation.

Non-enzymatic glycosylation is responsible for a number of biological effects, for instance for the inactivation of proteins, inhibition of the binding of regulatory molecules, trapping of soluble proteins by glycosylated extracellular proteins, reduction of protein degradation, abnormal DNA function, possible immunogenic effect and tissue toxicity and crosslinking of glycosylated proteins. The multiplicity of biological effects influenced by non-enzymatic glycosylation allows the pathological relevance of non-enzymatic glycosylation to be recognised.

Pathological changes which can be caused by non-enzymatic glycosylation are, for example, osteoarthritis, stroke, high blood pressure, peripheral vascular diseases and joint stiffness.

On account of the crosslinking of glycosylated proteins, however, non-enzymatic glycosylation is also responsible, for example, for the development of diabetic late damage and age-related changes.

The crosslinking of long-lived proteins such as, for example, collagen, crystalline, elastin and myelin increases in humans and animals with increasing age. As exemplified by the crosslinking of collagen, it was possible to show that in the syndrome of diabetes mellitus the age-related increase in the "crosslinks" is distinctly accelerated. These observations led to the hypothesis that the increased formation of crosslinks by collagen and other extracellular matrix proteins and the like is responsible for the development of physical changes of membranes during aging and for chronic complications in diabetes. These age-related changes of membranes in the central nervous system may be the cause of learning and memory disorders, which lead to the deterioration of mental activity. Learning and memory disorders are found, in particular, in Alzheimer's disease, but also in multi-infarct dementia and "benign forgetfulness in the elderly". Diabetic late damage includes, among other things, neuropathy, nephropathy, retinopathy, cataract, atherosclerosis/arteriosclerosis, coagulopathy, osteoporosis and decreased elasticity of the connective tissue. It can be assumed from intensive investigations that the central pathological findings of diabetes are caused by the formation, which is accelerated by hyperglycaemia, of the late end-products of the non-enzymatic glycosylation reaction in the tissue. In non-enzymatic glycosylation, a non-enzymatic addition of reducing or reactive sugars, principally glucose, takes place on the free amino groups of proteins. Short-lived proteins (such as, for example, enzymes, albumens and apoproteins) with a half-life of days or weeks react with reducing or reactive sugars, such as glucose, with the formation of a Schiff's base, the rate of formation of the Schiff's base being dependent on the glucose concentration in the blood:

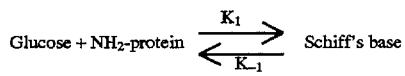

The unstable Schiff's bases then rearrange within a few hours to weeks to the more stable, but reversible Amadori products. Finally, a blood glucose-dependent equilibrium is established between Schiff's base and Amadori product:

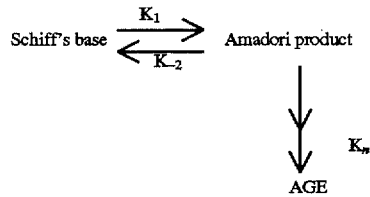

Some of the early glycosylation products of collagen or other long-lived proteins of the vascular wall experience a slow complex series of conversion reactions, which finally leads to the formation of irreversible late glycosylation end-products. These irreversible late glycosylation end-products are designated above and below as AGEs ("advanced glycosylation end-products"). These AGEs no longer disappear when the blood glucose level is corrected, but they accumulate continually during the entire lifetime of the vascular wall protein and lead to significant structural and functional changes in the vascular wall.

However, non-enzymatic glycosylation is not only restricted to proteins. Nucleic acids too, such as, for example, DNA, can also react with reducing or reactive sugars, in particular with glucose, in the presence of amino acids. Glucose-DNA products of this type may be responsible for the varied age-related changes in the genetic material, for instance for age-related damage to the central nervous system (CNS).

The AGEs are mostly fluorescent brown pigments, which can be detected both in vitro and in vivo. On account of the brown colour of the AGEs, non-enzymatic glycosylation, for example, is also designated as the non-enzymatic browning reaction.

For the abovementioned reasons, medicinal influencing of non-enzymatic glycosylation plays an outstanding role. Substances which intervene in the early phase of non-enzymatic glycosylation could thus also influence the formation of AGEs. It was possible for in vitro and in vivo investigations to show an effect of this type for aminoguanidine. The effects of the compounds of the formula I to be used according to the invention are to date superior to those of aminoguanidine.

The compounds of the formula I and their pharmacologically acceptable acid addition salts are therefore suitable as pharmacological active compounds, in the form of individual compounds or in the form of mixtures with one another, in particular for the control, alleviation and prevention of damage or diseases in humans and animals which are caused by non-enzymatic glycosylation, for instance for the control or prevention of osteoarthritis, stroke, high blood pressure, peripheral vascular diseases, joint stiffness, diabetic late damage (i.e., for example, neuropathy, nephropathy, retinopathy, cataract, atherosclerosis/arteriosclerosis, coagulopathy, osteoporosis and decrease in the elasticity of the connective tissue), for the control or prevention of age-related changes and age-related changes in the central nervous system, such as, for example, learning and memory disorders, age-related dementia and Alzheimer's disease.

The compounds of the compounds I to be used according to the invention and their pharmacologically acceptable acid addition salts can therefore be administered to humans as medicines per se, in mixtures with one another or in the form of pharmaceutical preparations which permit enteral or parenteral use and which contain as active constituent an effective dose of at least one compound of the formula I or of an acid addition salt thereof, in addition to one or more customary pharmaceutically innocuous excipients, fillers or diluents and, if appropriate, one or more additives.

The medicines can be administered orally, for example in the form of tablets, film tablets, coated tablets, hard and soft gelatine capsules, microcapsules, granules, powders, pellets, solutions, syrups, emulsions, suspensions, aerosols, foams, pills or pastilles. However, administration can also be carried out rectally, for example in the form of suppositories, or parenterally, for example in the form of injection solutions, or percutaneously, for example in the form of ointments, creams, gels, pastes, aerosols, foams, powders, tinctures, liniments or so-called transdermal therapeutic systems (TTS).

The pharmaceutical preparations can be prepared in a manner known per se using pharmaceutically inert inorganic or organic auxiliaries, excipients, fillers or diluents. For the preparation of pills, tablets, film tablets, coated tablets and the pellet or granule fillings of hard gelatine capsules, calcium phosphates, lactose, sorbitol, mannitol, starches, prepared starches, chemically modified starches, starch hydrolysates, cellulose, cellulose derivatives, synthetic polymers, talc, etc., for example, can be used. Excipients or diluents for soft gelatine capsules and suppositories are, for example, fats, waxes, semi-solid and liquid polyols, natural or hardened oils, etc. Suitable excipients or diluents for the preparation of solutions and syrups are, for example, water, polyols, solutions of sucrose, invert sugar, glucose, etc. Suitable excipients for the preparation of injection solutions are, for example, water, alcohols, glycerol, polyols or vegetable oils. Suitable excipients or diluents for ointments, creams and pastes are, for example, natural petroleum jelly, synthetic petroleum jelly, viscous and mobile paraffins, fats, natural or hardened vegetable and animal oils, neutral oils, waxes, wax alcohols, polyethylene glycols, polyacrylic acid, silicone gels, etc.

In addition to the active compounds and diluents, fillers or excipients, the pharmaceutical preparations can additionally contain, in a manner known per se, one or more additives or auxiliaries, such as, for example, disintegrants, binders, glidants, lubricants, release agents, wetting agents, stabilisers, emulsifiers, preservatives, sweeteners, colourants, flavourings or aromatisers, buffer substances, and also solvents or solubilisers, solution accelerators, antifoams, salt-forming agents, gel-forming agents, thickeners, flow regulators, sorbents, agents for achieving a depot effect or agents, in particular salts, for changing the osmotic pressure, coating agents or antioxidants, etc. They can also contain two or more compounds of the formula I or their pharmacologically acceptable acid addition salts and additionally one or more other therapeutically active substances.

Other therapeutically active substances of this type may be, for example: β-receptor blockers, such as, for example, propranolol, pindolol, metoprolol; vasodilators, such as, for example, carbocromene; tranquillisers, such as, for example, barbituric acid derivatives, 1,4-benzodiazepines and meprobamate; diuretics, such as, for example, chlorothiazide; cardiotonic agents, such as, for example, digitalis preparations, hypotensive agents, such as, for example, hydralazine, dihydralazine, prazosin, clonidine, Rauwolfia alkaloids; agents which reduce the fatty acid level in the blood, such as, for example, bezafibrate, fenofibrate; and agents for thrombosis prophylaxis, such as, for example, phenprocoumon.

The content of the active compound or the active compounds of the formula I in the pharmaceutical preparations can vary within wide limits and is, for example, 0.5 to 90% by weight, preferably 1 to 50% by weight. In solid administration forms, such as coated tablets, tablets, etc., the content of one or more active compounds of the formula I is in many cases 2 to 80% by weight. Liquid administration forms, such as drops, emulsions and injection solutions often contain 0.5 to 20% by weight, preferably 0.5 to 10% by weight, of one of more active compounds of the formula I. The content of one or more active compounds of the formula I can optionally be partially replaced in the pharmaceutical preparations, for example up to 50% by weight, preferably to 5 to 40% by, weight, by one or more other therapeutically active substances.

The dose can vary within wide limits and is to be suited to the individual conditions in each individual case. In general, in the case of oral administration, a daily dose of about 1 to 1000 mg, preferably 10 to 400 mg, per human individual is adequate. In the case of other administration forms too, the daily dose is in similar ranges of amounts. The daily dose can be divided into several, for example 2 to 4, part administrations.

If the compounds of the formula I have not already been described in the literature, compare, in particular, DE-A1-3,329,028, Examples 1b, 2b, 4b, 9 to 20, they can be easily synthesised by the preparation processes known for this class of compound. Thus, the compounds of the formula I can be prepared, for example, by introduction of compounds R-Cl, Where R has the meaning given in formula I, into excess 1,2-diaminoethane and subsequent heating, compare DE-A1-3,329,028, Example 9. They can also be prepared by hydrolysis of piperazin-2-ones substituted in the 3-position by R, compare DE-A1-3,329,028, page 14 and Examples 1b4, 2b2 and 4b, and also Arzneim.-Forsch./Drug Res. 35 (I), 1 (1985).

The following examples relate to pharmaceutical preparation forms.

EXAMPLE A

Soft gelatine capsules, containing 100 mg of active compound per capsule:

|  | per capsule |
| --- | --- |
| Active compound | 100 mg |
| Triglyceride mixture fractionated from coconut fat | 400 mg |
| Capsule contents | 500 mg |

EXAMPLE B

Injection solution, containing 20 mg of active compound per ml:

|  | per ml |
| --- | --- |
| Active compound | 2.0 mg |
| Polyethylene glycol 400 | 5.0 mg |
| Sodium chloride | 2.7 mg |
| Water for injection purposes | to 1 ml |

EXAMPLE C

Emulsion, containing 60 mg of active compound per 5 ml:

|  | per 100 ml of emulsion |
| --- | --- |
| Active compound | 1.2 g |
| Neutral oil | q.s |
| Sodium carboxymethylcellulose | 0.6 g |
| Polyoxyethylene stearate | q.s |
| Glycerol, pure | 0.2 to 2.0 g |
| Flavouring | q.s |
| Water (demineralised or distilled) | to 100 ml |

EXAMPLE D

Rectal medicaments, containing 40 mg of active compound per suppository:

|  | per suppository |
| --- | --- |
| Active compound | 40 mg |
| Suppository base | to 2 g |

EXAMPLE E

Tablets, containing 40 mg of active compound per tablet:

| | per tablet |
|---|---|
| Active compound | 40 mg |
| Lactose | 600 mg |
| Maize starch | 300 mg |
| Soluble starch | 20 mg |
| Magnesium stearate | 40 mg |
| | 1000 mg |

EXAMPLE F

Coated tablets, containing 50 mg of active compound per coated tablet:

| | per coated tablet |
|---|---|
| Active compound | 50 mg |
| Maize starch | 100 mg |
| Lactose | 60 mg |
| Sec. calcium phosphate | 30 mg |
| Soluble starch | 5 mg |
| Magnesium stearate | 10 mg |
| Colloidal silica | 5 mg |
| | 260 mg |

EXAMPLE G

The following recipes are suitable for the preparation of the contents of hard gelatin capsules:

| | | |
|---|---|---|
| a) | Active compound | 100 mg |
| | Maize | 300 mg |
| | | 400 mg |
| b) | Active compound | 140 mg |
| | Lactose | 180 mg |
| | Maize starch | 180 mg |
| | | 500 mg |

EXAMPLE H

Drops can be prepared according to the following recipe (100 mg of active compound in 1 ml=20 drops):

| | |
|---|---|
| Active comopound | 10 g |
| Methyl benzoate | 0.07 g |
| Ethyl benzoate | 0.03 g |
| Ethanol, 96% strength | 5 ml |
| demineralised water | to 100 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Pharmaceutical composition for inhibiting the formation of advanced glycosylation end products of proteins, comprising a mixture of an effective amount of a 2-(N-(2-aminoethyl)acetic acid derivative of the formula I

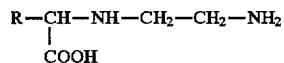

in which R denotes phenyl, thienyl, furyl, pyridyl, pyrrolyl, imidazolyl or thiazolyl, or phenyl, thienyl, furyl, pyridyl, pyrrolyl, imidazolyl or thiazolyl which is monosubstituted or polysubstituted by halogen, alkyl, alkoxy, dialkylaminoalkoxy or alkoxyalkoxy, or a pharmacologically acceptable salt thereof or several compounds of this type as an active compound or active compounds, together with one or more pharmaceutically acceptable excipients.

2. Pharmaceutical preparation according to claim 1, in which R denotes phenyl, thienyl, furyl, pyridyl, pyrrolyl, imidazolyl or thiazolyl which is mono substituted or polysubstituted by halogen, ($C_1$–$C_4$)alkyl, ($C_1$–$C_4$)alkoxy, di($C_1$–$C_4$) alkylamino-($C_1$–$C_4$) alkoxy or ($C_1$–$C_4$)alkoxy-($C_1$–$C_4$)alkoxy.

3. Pharmaceutical preparation according to claim 1, in which R denotes 2-thienyl.

* * * * *